United States Patent [19]

Bailey, Jr.

[11] 4,379,626

[45] Apr. 12, 1983

[54] FACILITY FOR CONDUCTING OPHTHALMOLOGICAL EXAMINATIONS

[76] Inventor: Paul F. Bailey, Jr., 4885 NW. Barnes Rd., Portland, Oreg. 97210

[21] Appl. No.: 196,261

[22] Filed: Oct. 14, 1980

[51] Int. Cl.³ .............................................. A61B 3/00
[52] U.S. Cl. ..................................... 351/200; 351/222
[58] Field of Search ................... 351/1, 17, 30, 37, 38; 52/36, 205

[56] References Cited

U.S. PATENT DOCUMENTS

| | | | |
|---|---|---|---|
| 1,600,017 | 9/1926 | Simonson | 52/79.1 |
| 2,248,199 | 7/1941 | Reyniers . | |
| 2,882,835 | 4/1959 | Buchanan . | |
| 3,233,346 | 2/1966 | Cornberg . | |
| 3,517,468 | 6/1970 | Woods | 52/79.1 |
| 3,553,911 | 1/1971 | Morrow et al. | 52/28 |
| 3,862,525 | 1/1975 | Greenspan | 52/64 |
| 3,923,134 | 12/1975 | Rezazadeh . | |
| 3,942,420 | 3/1976 | Marino . | |

Primary Examiner—R. A. Rosenberger
Attorney, Agent, or Firm—Kolisch, Hartwell & Dickinson

[57] ABSTRACT

A facility for conducting ophthalmological examinations or tests on a plurality of patients, includes, in a preferred embodiment, a first examining station defined by a room having an opening provided in one wall thereof used in conjunction with a second examining station defined by a room also provided with an opening in one wall thereof opposed laterally to the first examining station. A display device, such as a screen is disposed inside the second examining station for displaying test indicia to be visually perceived by a first patient situated in the first examining station. Test indicia are projected onto the screen by means of an acuity projector disposed in the first examining station. Additionally, the facility may further include a second display screen disposed inside the first examining station for displaying test indicia to be visually perceived by a second patient situated in the second examining station.

6 Claims, 4 Drawing Figures

FACILITY FOR CONDUCTING OPHTHALMOLOGICAL EXAMINATIONS

BACKGROUND AND SUMMARY OF THE INVENTION

The present invention relates to medical facilities such as ophthalmological offices, and more particularly to a novel facility for conducting eye examinations especially adapted for modular construction.

An example of a conventional ophthalmological office includes one or more examining rooms, generally of enclosed square or rectangular dimension. A patient chair is disposed adjacent one wall of an examining room and oppositely therefrom is positioned a screen. A device, called an acuity projector, is generally positioned adjacent the patient chair and includes a series of images, such as alphabetical letters, which may be selectively directed toward and projected onto the screen by suitable actuation of the ophthalmologist. The letters are for viewing by the patient so that the ophthalmologist can determine the patient's visual perception. Another instrument, known as a refractor is positionable in front of the patient's eyes and is provided so that the ophthalmologist may selectively insert, retract and exchange various lenses in order to determine the proper correction needed for the patient.

The above type of examining room may require that the screen be positioned approximately twenty feet away from the patient chair so that the patient's vision is determined according to a twenty foot standard. Alternatively, the use of mirrors may permit the screen to be positioned closer to the patient chair but it still must be appreciated that the location of the screen is somewhat distant, i.e. ten feet or so, from the patient. Eye examinations using the acuity projector and screen are conducted in darkness and it is therefore conventional for the screen to be disposed within the examining room for viewing by the patient. Of course, it can be appreciated that the screen is not necessary for all eye tests which an ophthalmologist may perform but, nevertheless, the screen is conventionally disposed within the examining room. Because of the required distance between the screen and the patient, an examining room must be oversized, that is, its square foot area is large only because it is necessary to provide the screen within the examining room. The actual space required for the patient chair, acuity projector and refractor is relatively small—it need only be large enough to comfortably accommodate the patient and ophthalmologist.

Proposals have been made to decrease the size of an examining room while still maintaining location of a screen therewithin. For instance, one example contemplates that an examining room be formed of generally L-shaped configuration so that the screen is disposed at the end of an "alley" which may be thought of as one of the legs of an "L". Another proposal contemplates that a tube extends outwardly from an end wall of an examining room with the screen being positioned at the end of the tube. While this latter proposal may provide for a smaller examining room, it should be appreciated that provision of an extending tube may interfere with other portions of the ophthalmologist's office or will be disposed outwardly from the exterior of a building providing a rather odd and cumbersome construction.

Accordingly, it is a general object of the present invention to provide a facility for conducting ophthalmological tests which includes laterally opposed and separate first and second examining stations each of which is defined by a room having an opening provided in one wall thereof. A first display means, such as a screen is disposed inside the second examining station for displaying test indicia to be visually perceived by a first patient situated or seated in the first examining station. A second display means, such as a screen, may be disposed inside the first examining station for displaying test indicia to be visually perceived by a second patient situated or seated in the second examining station. Each of the patients, during a visual acuity test, may look through an opening provided in the wall of an associated examining station for viewing the screen which is disposed inside the opposite examining room.

Another object of the present invention is to provide a facility, such as described above, in which each of the screens is disposed within an isolating means such as an enclosure or compartment for isolating each of the screens from the examining station in which it is positioned inside while permitting viewing from a patient situated in the opposite examining station. Each of the compartments includes a window presented toward and substantially aligned with the opening of the opposite examining station. Thus, it should be appreciated that the actual internal space occupied by an examining room may be greatly diminished from that provided in prior art examining rooms because the screen is positioned inside an opposed examining station but isolated from viewing therefrom.

Still another object of the present invention is to provide a facility, such as described above, in which each of the compartments is positioned substantially interiorly into its associated examining station. Further, it is contemplated that each of the examining stations is separated by a corridor means such as a hallway interposed therebetween so that an ophthalmologist may have ready access between the examining stations.

Yet a further object of the present invention is to provide examining stations, such as described above, which may be readily built according to modular construction. Stated differently, it is an object of the present invention to construct the examining stations as modules (of any predetermined number) which may be interconnected and positioned within a larger office space. The area or region outside of the modules may be suitably retained for other functions required in an ophthalmolgost's office, such as a waiting room bookkeeping area, chart and records area, etc.

These and additional objects and advantages of the present invention will be more readily understood from a consideration of the drawings and the following detailed description of the preferred embodiment.

DETAILED DESCRIPTION OF THE PREFERRED EMBODIMENT

Figure 1:
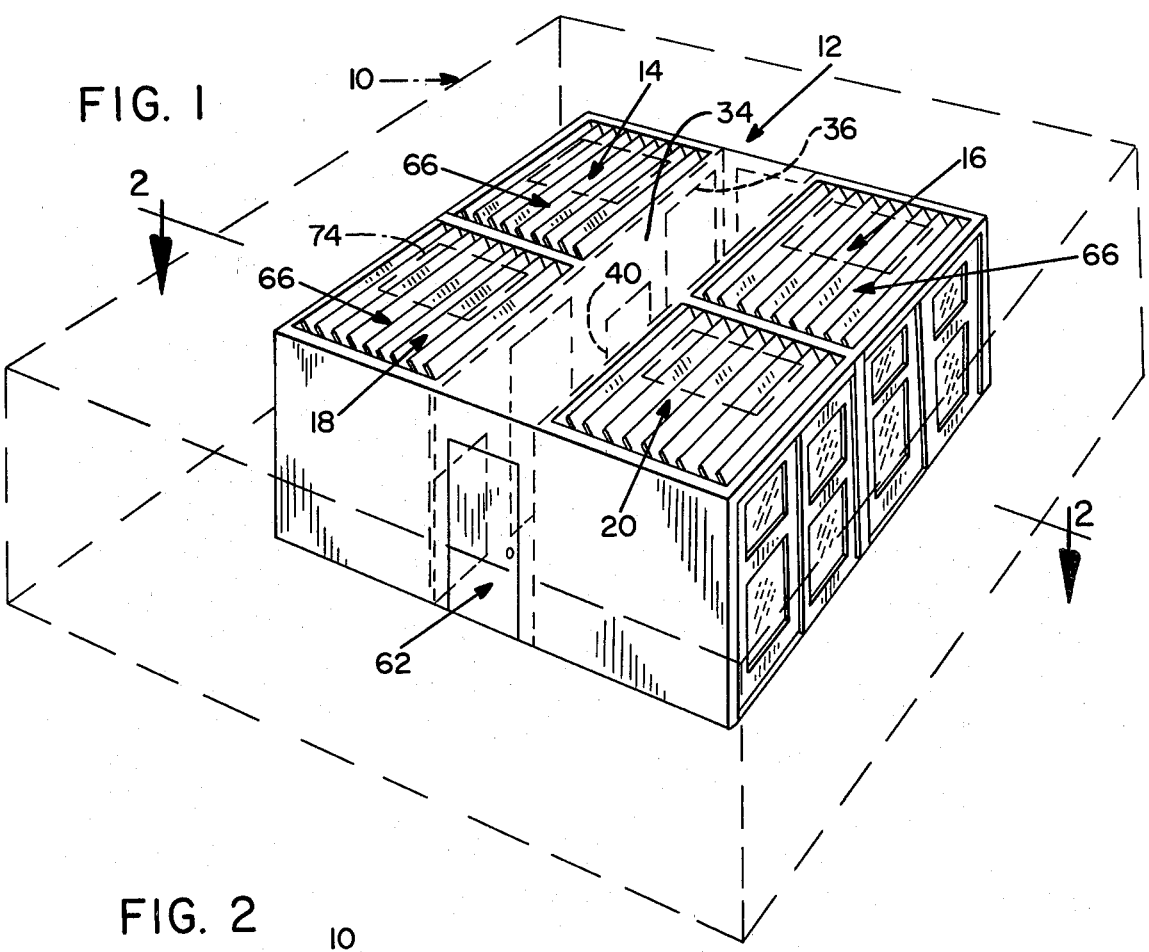
FIG. 1 is a perspective view of a facility according to the present invention and illustrates a plurality of examining stations, formed as modules disposed within a larger interior office space indicated in dashed outline.

As mentioned previously, it is a general object of the present invention to provide examining stations which may be formed as modules opposed from one another so that by disposing a screen inside one of the examining stations, for viewing by a patient situated in the opposed examining station, a substantial decrease in the size of the examining station may be realized. With the decrease in examining station size, each of the examining stations may be formed as a module for positioning in a larger external office space. For instance, as can be seen with reference to FIG. 1, an exterior office space or volume is generally indicated in dashed or broken outline at 10 within which is mounted a series of modules generally indicated at 12. Each of the modules may be formed as a box-like room which serves as an examining station. For example, FIG. 1 shows a total of four examining stations, such as first, second, third and fourth examining stations generally indicated at 14, 16, 18 and 20 respectively. While a total of four examining stations are shown in FIG. 1, it should be appreciated that any predetermined number may be provided in the interior region of an office space depending upon the actual volume of the office space and an ophthalmologist's requirements.

Figure 2:
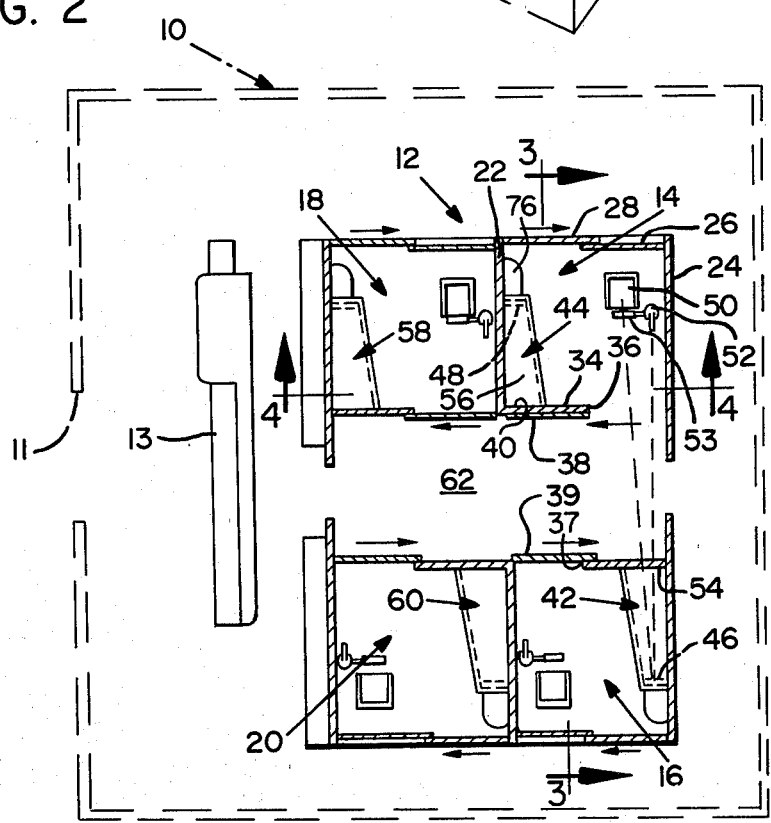
FIG. 2 is a top plan view of the facility shown in FIG. 1.

With reference now directed to FIG. 2 as well as FIG. 1, a description of the relationship between first examining station 14 and second examining station 16 will be set forth. The construction of the third and fourth examining stations is substantially identical. With respect to first examining station 14, it can be seen that it includes a pair of spaced-apart upstanding panels or walls indicated at 22, 24 with an end wall indicated at 26. A slidable door is indicated at 28 for permitting patient ingress and egress. End wall 26 and slidable door 28 are provided with windows of suitable darkened shade. The construction of end wall 26 and slidable door 28 may be best appreciated from a consideration of FIG. 4. As shown, end wall 26 may be formed as a panel provided with window panes such as indicated at 30 and slidable door (shown in closed position) is provided with window panes such as shown at 32. Third examining station 18 is substantially identical in construction and wall 22 is common to both the first and third examining stations.

Returning to a consideration of FIG. 2, it can be seen that another end wall, indicated at 34, is provided in the modular construction of first examining station 14 (see also FIG. 1) and includes a large opening indicated at 36. Another movable or slidable door, not provided with window panes, is indicated at 38 (not shown in FIG. 1). Door 38 may be suitably positioned to open or close opening 36 and is suitably mounted on runners or guides (not shown). Additionally, it can be seen from a consideration of FIG. 1 that another opening or window indicated at 40 is formed in end wall 34. Window 40 is an opening presented into a compartment, to be hereinafter described, which holds a display means such as a screen. Second examining station 16 includes an opening 37 and a slidable door 39.

For instance, as shown in FIG. 2, second examining station 16 is formed as a module substantially identical to first examining station 14 and includes a first isolating means 42. A second isolating means is indicated at 44 disposed inside first examining station 14 and it is to be appreciated that each is provided for mounting a display means such as a screen therewithin. Explaining further, it can be seen that a first display means indicated at 46 is mounted internally of first isolating means 42 and a second display means 48 is mounted internally of second isolating means 44 (see also FIG. 4). The purpose of the first and second display means is to provide screens which will receive projections of test indicia, such as alphabetical letters, projected from an examining station. For instance, first examining station 14 is provided with a patient chair 50 upon which a first patient may be situated or seated and an acuity projector indicated at 52. A refractor is shown as 53. Thus, first display means 46, mounted internally of first isolating means 42 and disposed inside second examining station 16 is provided for displaying test indicia (originating from acuity projector 52) to be visually perceived by a first patient situated in first examining station 14.

Figure 4:
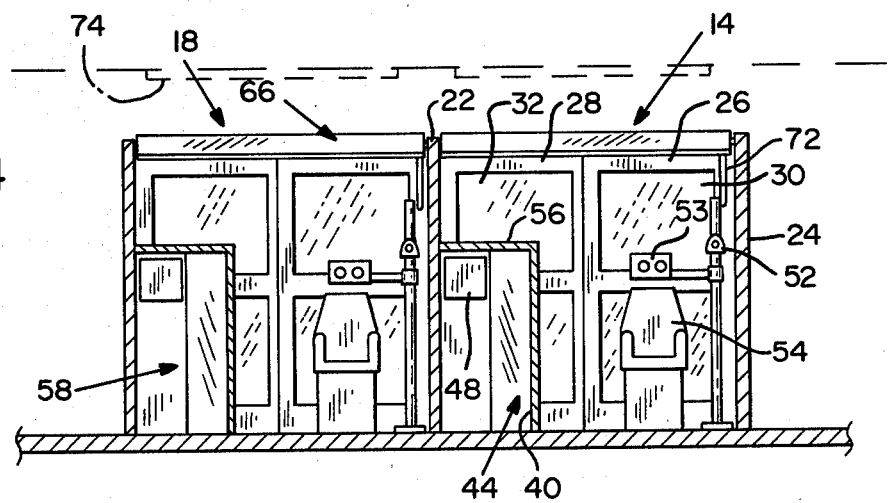
FIG. 4 is a view taken along lines 4—4 of FIG. 2.

Similarly, second display means 48, mounted internally of second isolating means 44, is disposed inside first examining station 14 for displaying test indicia to be visually perceived by a second patient situated or seated in the second examining station. It should be appreciated that each of the isolating means is provided for isolating its associated display means from being viewed by a patient situated in its adjacent examining station. Elaborating further, it can be seen that first isolating means 42 is constructed as a box-like walled compartment which may be thought of as a "tunnel," within which is mounted first display means 46. As shown in FIG. 4, second isolating means 44 is also formed as a box-like compartment or "tunnel" within which is mounted second display means 48. Each of the isolating means is provided with a window (such as shown at 40 in FIGS. 1 and 4) presented toward and substantially aligned with the opening of its opposed examining station. Thus, it can be seen that first isolating means 42, provided with a window 54 is oriented in second examining station 16 so that the window is presented toward and substantially aligned with opening 36 of first examining station 14. Similarly, second isolating means 44 (see also FIG. 4) is provided with window 40 (see also FIG. 1) which is presented toward and substantially aligned with opening 37 of second examining station 16.

Additionally, it is to be noted that each of the first and second isolating means is positioned substantially interiorly of its associated examining station in order to provide optimal utilization into space. Furthermore, each of the first and second isolating means includes an upper wall surface (such as indicated at 56 in FIG. 4) which is disposed beneath the ceiling of its associated examining station. Because each of the display means need only be as high, relative to a floor surface, as the height of a seated patient's head, it is only required that the top wall surface of each isolating means extend only slightly thereabove. This configuration can be best appreciated from a viewing of FIG. 4. The top wall surface of each isolating means may serve as a convenient shelf for stowing lenses, equipment, etc.

This, in brief summary to this point, it can be seen that there has been described a facility in which a first examining station defined by a room or module having an opening provided in one wall thereof is opposed laterally from a second examining station defined by a room or module also provided with an opening in one wall thereof. While it is not deemed necessary to provide a detailed description of third and fourth examining stations 18, 20 respectively, it can be seen that they are disposed, relative to one another, similarly to the orientation of the first and second examining stations. However, as can be appreciated from a viewing of FIGS. 1 and 2, the third and fourth examining stations are positioned in side by side relationship relative to the first and second examining stations, respectively. Further, it can be seen that third examining station 18 includes an isolating means indicated at 58 and fourth examining station 20 includes an isolating means indicated at 60. Each of isolating means 58, 60 is provided with a suitable display means, such as described with reference to first and second display means 42, 44 for viewing by patients disposed in the third and fourth examining stations.

Figure 3:
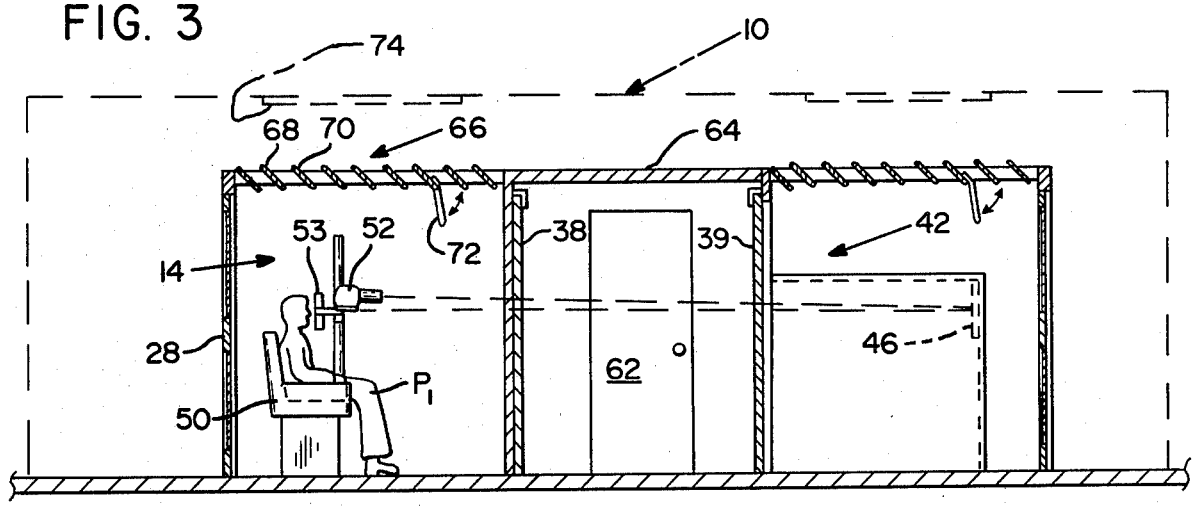
FIG. 3 is a side elevation view taken along lines 3—3 of FIG. 2 and illustrates a pair of opposed examining stations isolated for showing certain features of the facility.

An additional feature of the present invention resides in the use or employment of a corridor means or hallway such as indicated at 62 in FIG. 2 (see also FIG. 3). The hallway is provided for permitting access between the various examining stations by an ophthalmologist. It is contemplated that the hallway will be provided with a covered or enclosed ceiling such as indicated at 64 in FIG. 3. A suitable ligh source (not shown) may be provided for selectively illuminating hallway 62. In contradistinction, it is to be noted that each of th examining stations is provided with a ceiling construction which includes a movable means selectively operable for permitting and preventing light to be admitted into each examining station from an external light source. As shown in FIG. 3, a movable means generally indicated at 66 includes a plurality of linked shutters or louvers, such as indicated at 68, 70.

The louvers may be simultaneously deployed in an examining station by use of an actuating means, such as a handle shown at 72, so that they may be opened (as shown in FIG. 3) to permit light from the external room to be admitted into an examining station such as first examining station 14. As mentioned previously, it is sought by the present invention to provide a plurality of examining stations which are compact modules. As such, it can be seen from a consideration of FIG. 3 that light may be directed from a light source (schematically indicated at 74) provided in the ceiling of the external room. Closure of the louvers will darken an examining station. Lastly, it is to be noted that small seats or stools may be affixed to an end wall of the isolating means— one such seat being shown at 76 in FIG. 2.

A brief description will now be set forth describing how the facility of the present invention may be advantageously used by an ophthalmologist in conducting tests on a plurality of patients. Only the use of first examining station 14 and second examining station 16 will be set forth, but it may be readily appreciated that a similar procedure may be utilized with respect to the third and fourth examining stations. Initially, a patient walks into external office 10 through doorway 11 and advises a nurse or secretary positioned at counter 13 of an appointment. The patient is then directed into first examining station 14 (door 28 being suitably shifted to the right as indicated in FIG. 2) and is seated in chair 50. As shown in FIG. 3, patient $P_1$ is now in position for ophthalmological testing. The ophthalmologist may then initially consult with the patient and it is assumed that louvers 68, 70 may be suitably opened so that first examining station 14 is illuminated. Slidable door 38 may be either opened or closed relative to opening 36.

After the initial consultation, a so-called refraction test may be performed. Door 38 is opened so that the patient may view through opening 36 and window 54 of first isolating means 42 test indicia projected onto the screen of first display means 46. During the refraction test, louvers 68, 70 are closed and hallway 62 is darkened. Test indicia are suitably projected from acuity projector 52 for display on first display means 46. The ophthalmologist may suitably vary the test indicia projected onto first display means 46 and also may selectively insert and retract various corrective lenses in refractor 53 in order to determine suitable correction for the patient's eyes. Of course, it can be appreciated that a second patient may be situated or seated in second examining station 16 and will be isolated from the test indicia display on second display means 46 because of the boxlike or compartment construction of first isolating means 42. After the refraction test has been completed on patient $P_1$, the ophthalmologist may then apply suitable eye drops into the patient's eyes in order to effect dilation of the pupils. The drops are required to be present in the patient's eyes for 20 to 30 minutes before a conventional pressure or glaucoma test may be conducted or other tests and analyses be made. During this time, it is advantageous to maintain louvers 68, 70 in a closed position so that the first examining station will remain substantially dark for patient eye comfort. However, because windows are provided in end wall 26 and slidable door 28, the patient (even though seated in a small room) may not necessarily feel totally isolated or uncomfortably enclosed in a small space.

The ophthalmologist may then exit through opening 36, close slidable door 38 and walk along hallway 62 into second examining station 16 by suitably sliding or shifting slidable door 39 to permit entry thereinto. Tests may then be conducted in a similar manner on a second patient situated in the second examining station. Similarly, the same or another ophthalmologist may be performing simultaneous tests in the third and fourth examining rooms. It is noted that slidable door 38 is shown covering window 40 of second isolating means 44. However, it is possible to suitably shorten the width of slidable door 38 so that both opening 36 and window 40 are unobstructed. The same may be said with respect to slidable door 39 and opening 37. Thus, it is possible to have patients situated in each of the first and second examining stations each undergoing a refraction test.

From the above, it should be seen that the facility of the present invention provides several important and distinct advantages. First of all, it is to be recognized that the facility enables the provision of rather small modules or examining stations by virtue of the fact that a display means for use in conjunction with an examining station is disposed inside a laterally opposed remote examining station. Therefore, it is not necessary to have a large room in which space is wasted only to accommodate provision of a screen or display means. Secondly, it can be seen that by providing isolating means, such as indicated at 42 for isolating first display means 46 from second examining station 16, the second examining station will not interfere with nor be interfered by ophthalmological tests being conducted in first examining station 14. Similarly, the same advantages are present with respect to second isolating means 44 being disposed inside first examining station 14. It is also important to note that it is preferably to dispose each of the isolating means substantially within an examining station for use by a laterally opposed examining station.

By constructing a facility as described above, a small station or room formed as a module may be provided. The modules may be suitably interconnected and disposed within a large external office. Furthermore, it is to be noted that separating opposed examining stations by a corridor which may be darkened, such as hallway 62, enables an ophthalmologist to easily travel from one examining station to another. By providing interior slidable doors, such as slidable doors 38, 39 each of the examining stations may be isolated as a unit from the other examining stations.

Still another advantage of the present invention resides in the use of a ceiling provided above each of the examining stations in which light may be selectively permitted to enter or be blocked from illuminating an examining stations. Of course, if the external office or space is provided with air conditioning, such conditioned air may be directed through the louvers as desired.

The important point to note is that the facility of the present invention utilizes the basic concept of providing a small examining station or module in which a display means unconnected and relatively remote from the module is positioned adjacent another opposed module.

While the present invention has been shown and described with reference to the foregoing preferred embodiment, it will be appreciated that other changes in form and detail may be made therein without departing from the spirit and scope of the invention as defined in the appended claims.

It is claimed and desired to secure by letters patent:

1. A facility for conducting ophthalmologist tests on a plurality of patients comprising:
   a first examining station defined by a room having an opening provided in one wall thereof;
   a second examining station defined by a room also provided with an opening in one wall thereof opposed laterally to said first examining station;
   first display means disposed inside said second examining station for displaying test indicia to be visually perceived by a patient situated in said first examining station;
   second display means disposed inside said first examining station for displaying test indicia to be visually perceived by a second patient situated in said second examining station;
   first isolating means for isolating said first display means from said second examining station including a window presented toward and substantially aligned with the opening of said first examining station; and
   second isolating means for isolating said second display means from said first examining station including a window presented toward and substantially aligned with the opening of said second examining station.

2. The facility of claim 1 wherein said first isolating means is defined by a compartment within which is mounted said first display means, said second isolating means also being defined by a compartment within which is mounted said second display means.

3. The facility of claim 2 wherein said first isolating means is positioned substantially interiorly into said second examining station, and said second isolating means is positioned substantially interiorly into said first examining station.

4. The facility of claim 3 wherein said first isolating means includes an upper wall surface disposed beneath the ceiling of said second examining station, and second isolating means includes an upper wall surface disposed beneath the ceiling of said first examining station.

5. The facility of claim 2 further including a covered corridor means interposed between said first and second examining stations.

6. The facility of claim 5 wherein movable means are disposed in the ceiling of said first and second examining stations each being selectively operable for permitting and preventing entry of light into said examining stations from a source external thereof.

* * * * *